United States Patent [19]

Schuster et al.

[11] 4,318,414
[45] * Mar. 9, 1982

[54] PROBE FOR OBTAINING CERVICAL MUCUS

[75] Inventors: Samuel R. Schuster, Wellesley; Louis Kopito; Harold Kosasky, both of Brookline, all of Mass.

[73] Assignee: Ovutime, Inc., Newton, Mass.

[*] Notice: The portion of the term of this patent subsequent to Jun. 12, 1996, has been disclaimed.

[21] Appl. No.: 46,669

[22] Filed: Jun. 8, 1979

Related U.S. Application Data

[63] Continuation-in-part of Ser. No. 795,097, May 9, 1977, Pat. No. 4,157,709.

[51] Int. Cl.³ ............................................ A61B 10/00
[52] U.S. Cl. .................................... 128/759; 128/269
[58] Field of Search ............................. 128/756–759, 128/269; 73/53

[56] References Cited

U.S. PATENT DOCUMENTS

| | | | |
|---|---|---|---|
| Re. 27,915 | 2/1974 | Kohl | 128/757 |
| 3,400,708 | 9/1968 | Scheidt | 128/757 |
| 3,513,830 | 5/1970 | Kalayjian | 128/759 |
| 3,640,268 | 2/1972 | Davis | 128/759 |
| 3,831,585 | 8/1974 | Brondy et al. | 128/757 |
| 3,961,620 | 6/1976 | Schack et al. | 128/757 |
| 4,027,658 | 6/1977 | Marshall | 128/757 |
| 4,136,680 | 1/1979 | Southworth | 128/759 |
| 4,157,709 | 6/1979 | Schuster et al. | 128/269 |

Primary Examiner—Robert W. Michell
Assistant Examiner—Francis J. Jaworski
Attorney, Agent, or Firm—Morse, Altman, Oates & Dacey

[57] ABSTRACT

The present invention features essentially only two relatively movable components, of which an outer sheath provides a forwardly curved path, a flexible mouth and a forwardly extending reference foot, and an inner flexible shaft has a forward element, which serves to open the mouth and to collect a mucus specimen when the flexible shaft moves forwardly and which serves to protect the mucus specimen and to close the mouth when the flexible shaft moves rearwardly.

A probe is provided for inserting a test element into the vaginal cavity while shielding it from intermediate vaginal contact, for positioning the test element precisely in contact with the cervical os in order to collect a specimen of cervical material therefrom, and for retrieving the test element and the specimen from the vaginal cavity while shielding them from intermediate vaginal contact.

14 Claims, 20 Drawing Figures

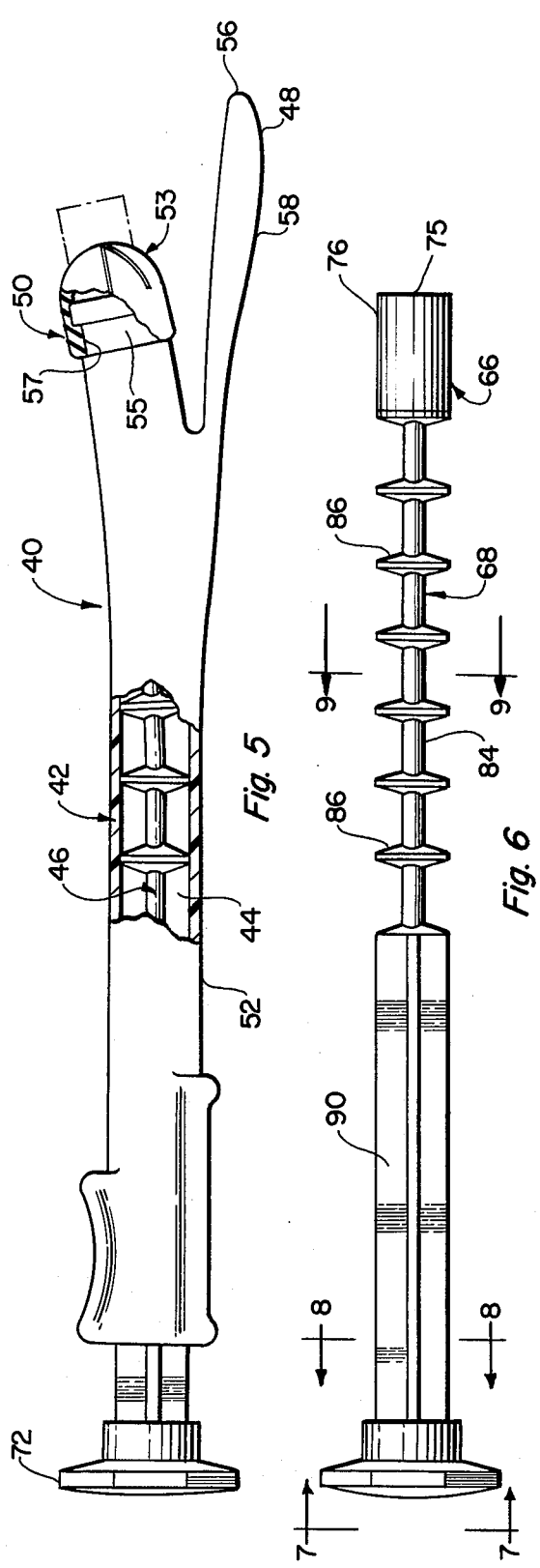
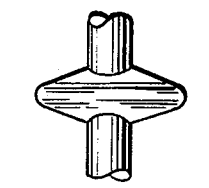
Fig. 10
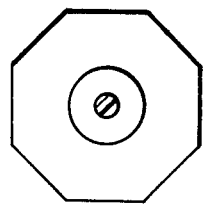
Fig. 9
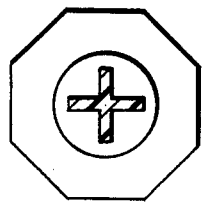
Fig. 8
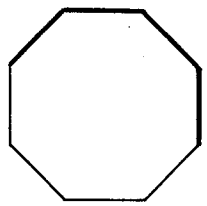
Fig. 7

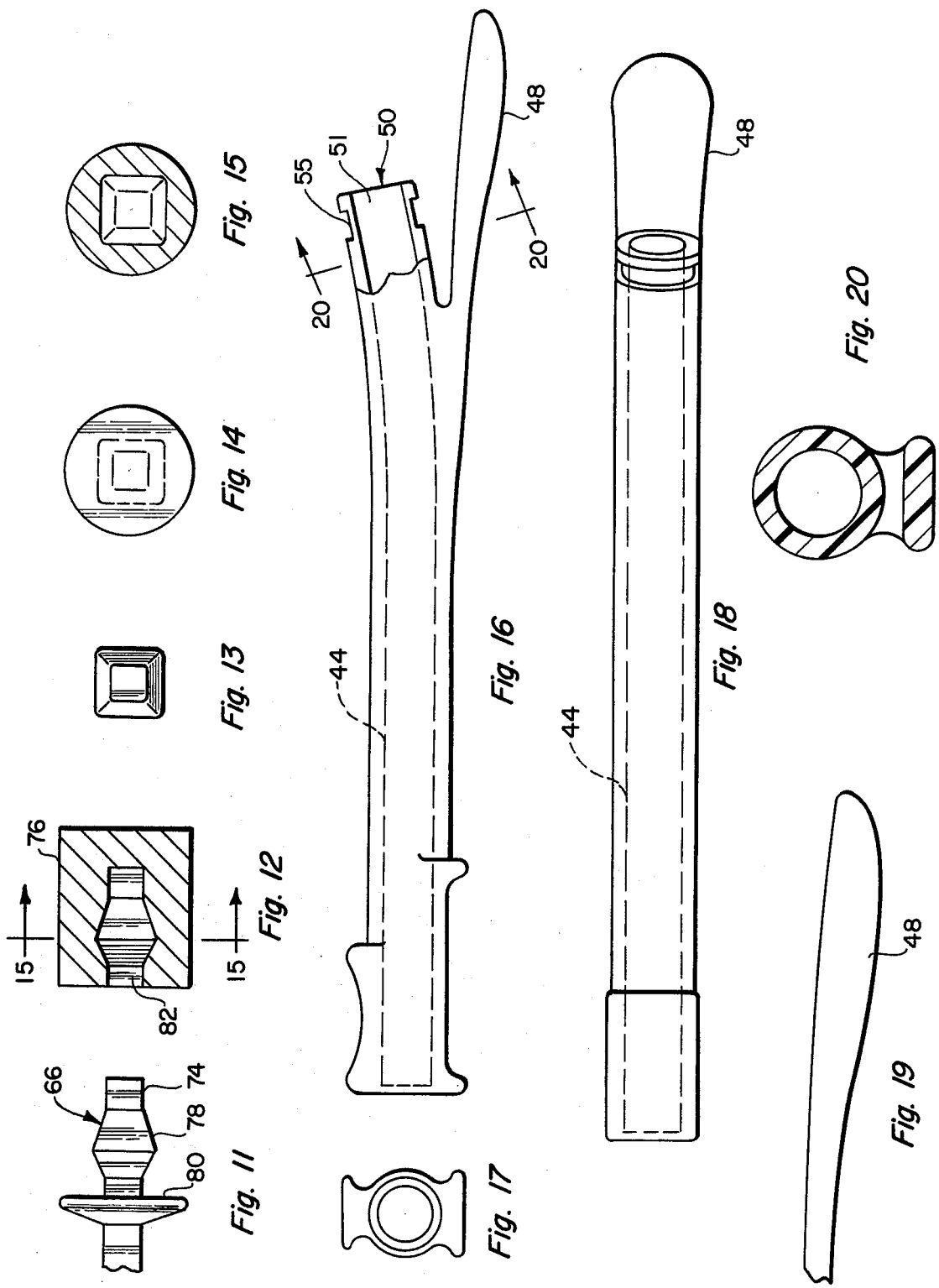

4,318,414

PROBE FOR OBTAINING CERVICAL MUCUS

RELATED APPLICATION

The present application is a continuation-in-part of application Ser. No. 795,097, filed May 9, 1977, now U.S. Pat. No. 4,157,709.

BACKGROUND OF THE INVENTION

1. Field of the Invention

The present invention relates to the medical testing of cervical material, i.e. tissue and/or mucus, and more particularly to the routine collection of cervical material via the vaginal cavity in such a way that the cervical specimen is unaffected by contact with the vaginal wall.

2. The Prior Art

In the past, it usually has required skill medical personnel to obtain useful samples of cervical material. In one form, such cervical material is tissue from the cervical os, which is tested for malignancy in the form of a pap smear. In another form, such cervical material is mucus from the cervical os, which indicates ovulation when a predeterminedly low viscosity and the absence of ovulation when of predetermined high viscosity, for fertility control. Previously proposed probes, by which cervical material may be collected, examined, and tested, generally have not been for self-use by women wishing to retrieve cervical specimens. It is desired to retrieve such cervical specimens by a reliable probe, which does not require a skilled medical operator, but rather which can be operated by the subject woman herself. The probe of the present invention thus enables any women to submit self-obtained cervical tissue specimens to the laboratory for microscopic examination or to subject self-obtained cervical mucus to rheological testing in simple equipment available in the home for fertility control.

BRIEF DESCRIPTION OF THE INVENTION

The primary object of the present invention is to provide a probe for inserting a test element into the vaginal cavity while shielding it from intermediate vaginal contact, for positioning the test element precisely in contact with the cervical os in order to collect a specimen of cervical material, and for retrieving the test element and the specimen from the vaginal cavity while shielding them from intermediate vaginal contact. The design of this probe is based in part upon two considerations. The first consideration is that, in most women, the distance between the cervical os and the posterior fornix is approximately the same, viz. 1 to 5 centimeters. The second consideration is that, in order to achieve the most accurate test results, it is often desirable that the cervical material be undisturbed by transfer from one mechanical device to another, for example, from a first test support to a second test support. It is desirable particularly that the collection of cervical mucus, which at times other than during mid-cycle is very sparse, may be made directly on the final test support. In accordance with the present invention, the probe preferably comprises a test element for collecting a specimen by direct contact with the cervical os, a sheath within which the test element is confined during insertion into the vaginal cavity, a foot at the forward extremity of the sheath, which enables repeated positioning of the sheath predeterminedly within the vaginal cavity, and a manual control for directing the test support from within the sheath into contact with the cervical os and from contact with the cervical os back into the sheath. Thus, removal of the instrument from the vaginal cavity achieves isolation of the test support within the sheath during removal of the sheath from the vaginal cavity. The present invention features essentially only two relatively movable components, of which an outer sheath provides a forwardly curved path, a flexible mouth and a forwardly extending reference foot, and an inner flexible shaft has a forward element, which serves to open the mouth and to collect a mucus specimen when the flexible shaft moves forwardly and which serves to protect the mucus specimen and to close the mouth when the flexible shaft moves rearwardly.

Other objects of the present inventions will in part be obvious and will in part appear hereinafter.

The invention accordingly comprises the devices and processes herein disclosed, together with their parts, steps and interrelationships, the scope of which will be indicated in the appended claims.

BRIEF DESCRIPTION OF THE DRAWINGS

For a fuller understanding of the nature and objects of the present invention, reference is made to the following detailed description, which is to be taken in connection with the accompanying drawings, wherein:

FIG. 5 is a longitudinal, partly cross sectional view of the device as shown in FIG. 2;

FIG. 6 is a longitudinal, side view of a component of the device of FIG. 2;

FIG. 7 is a cross-sectional view of the component of FIG. 6, taken substantially along the line 7—7, FIG. 8 is a cross-sectional view of the component of FIG. 6, taken substantially along the line 8—8;

FIG. 9 is a cross-sectional view of the component of FIG. 6, taken substantially along the line 9—9;

FIG. 10 is a fragmentary side view of a portion of the component of FIG. 6;

FIG. 11 is a fragmentary side view of a portion of the component of FIG. 6;

FIG. 12 is a cross-sectional view of an element forming part of the component of FIG. 6;

FIG. 13 is an end view of the portion of FIG. 11;

FIG. 14 is a front view of the element of FIG. 12;

FIG. 15 is a cross-sectional view of the element of FIG. 12, taken substantially along the line 15—15;

FIG. 16 is a side elevation of another component of the device of FIG. 2;

FIG. 17 is an end elevation of the component of FIG. 16;

FIG. 18 is a top view of the component of FIG. 16;

FIG. 19 is an enlarged fragmentary side view of a portion of the component of FIG. 16; and FIG. 20 is a cross-sectional view of the component of FIG. 16, taken substantially along the line 20—20.

DETAILED DESCRIPTION OF THE PREFERRED EMBODIMENTS

Figure 1:
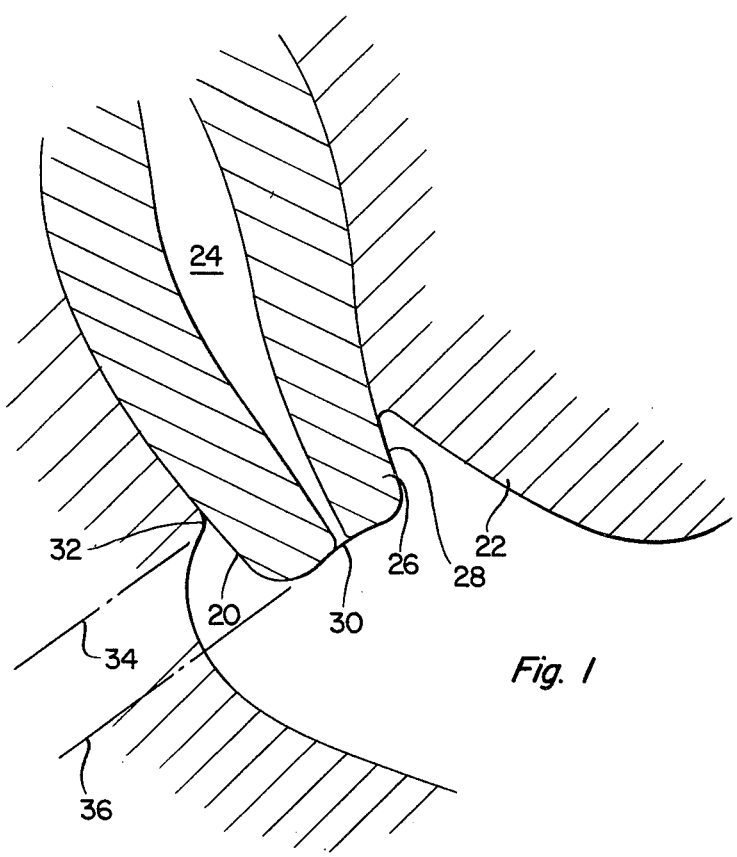
FIG. 1 is a sagittal view of the human female anatomy in the vicinity of the cervix.

FIG. 1 anatomically illustrates details of the uterus 20 and the vaginal wall 22. Uterus 20 includes the uterine fundus 24, the cervix 26, the portio vaginalis 28, and the cervical os 30. The posterior fornix 32 between the most distal portion of the portio vaginalis and the posterior vaginal wall is of particular interest in accordance with the present invention. It has been found that the geometrical distance, between a plane 34 containing the end of the posterior fornix and a plane 36 containing the cervical os, ranges from 1 to 5 centimeters in almost all normal women. The test probe now to be described relies upon that anatomical fact.

With reference now to FIGS. 2 through 5, the illustrated probe, shown generally at 40, comprises an outer sheath 42 and an inner shaft 46 slidable therewithin. Sheath 42 and shaft 46, in effect, are outer and inner telescoping members, both of which are predeterminally shaped to serve interrelated functions. The purpose of these interrelated functions is to collect mucus from the cervical os at the free end 75 of a test support 76, which is shown in FIGS. 6 and 12. This test support is in a form that is adapted for contact by a second element in such a way that the pulling force necessary to cause separation of the elements is a function of the rheological properties of the mucus. Such a system is described in detail in U.S. Pat. No. 3,926,037, issued Dec. 16, 1975, and U.S. Pat. No. 4,002,056, issued Jan. 11, 1977.

Sheath 42, which is composed of a thin semi-rigid polymer, such as polyethlyene or polyethylene terephthate, includes a forwardly projecting reference foot portion 48, a transversely shaped intermediate mouth portion 50, a rearwardly extending tubular body portion 52, and a rearward grip portion 54. Extending through sheath 42 is a passage 44 that is circular in cross-section and uniform in diameter in order to permit telescoping movement of shaft 46.

In accordance with the present invention, reference foot portion 48 ranges in length from 1 to 5 centimeters so that, when the instrument is inserted into the vagina, the reference foot portion moves along the inferior vaginal wall until seated in the posterior fornix, which serves as a reference point that limits further insertion. Reference foot portion 48 has a broadened rounded forward extremity 56 that is shaped to contact the end 32 of the posterior fornix, a convex under surface 58 that is shaped to rest against the posterior vaginal wall, and a concave upper surface 60 that is shaped to rest beneath the most distal portion of the portio vaginalis. Intermediate mouth portion 50 includes the forward open end portion 51 of the main body of sheath 40 and a removable cap 53. As shown in FIGS. 5 and 16, adjacent the extremity of end portion 51 is a circumferential groove 55. As shown in FIG. 5, cap 53 has an inner circumferential lip 57, which snugly seats in circumferential groove 55. Cap 50, which for example is composed of polyethylene or polyethylene terephthalate, is sufficiently flexible to permit lip 57 to be snapped into and out of groove 55. The forward wall of cap 50 is severed into six sections by three intersecting slits 61, 62, 64, which meet in the vicinity of the center of mouth portion 50. These severed sections constitute a closure with flexible flaps that tend to remain closed normally, but that can be opened from inside the sheath in a manner to be described below.

Shaft 46 includes a forward portion 66, including removable test support 76, an intermediate semi-rigid portion 68 capable of conforming to the curved shape of the forward portion of passage 44, a rearward rigid portion 9 capable of easing insertion of the forward and intermediate portions of the shaft into passage 44, and a rearmost handle 72 for engagement by the hand of an operator. As shown in FIGS. 11 to 15, the forward end of shaft 46 includes a tip 74 of relatively small diameter, a bevelled circumferential rib 78 of slightly larger diameter, and a circumferential shoulder 80. Test support has an opening 82 with portions that correspond in shape and position to forward tip 74, circumferential rib 78, and stop 80 so that test element 76 can be snapped securely onto the end portion of shaft 46 and removed readily therefrom. Intermediate semi-rigid portion 68 has an axial spine 84, along which are positioned a plurality of spaced beads 86. Rearward rigid portion 70 includes four longitudinal splines 90, spaced ninety degrees apart. The diameters of test support 76, across beads 86, and across splines 90 all are approximately the same, i.e. slightly smaller than the diameter of passage 44.

In the preferred configuration with respect to the axis of the rearward portion of sheath 42, the axis of mouth 50 is disposed at approximately a 12 degree angle in one polar direction; the axis of reference 48 is disposed at approximately a 4 degree angle in the other polar direction; and the length from the rearward extremity of sheath 42 to the forward tip of reference 48 is approximately 7.03 inches (17.6 centimeters). length from the rearward extremity of sheath 42 to the The remaining dimensions can be ascertained by examination of the drawings.

OPERATION

Figure 2:
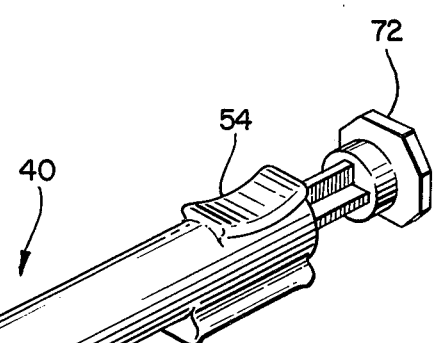
FIG. 2 is a perspective view of a device embodying the present invention in a first operating condition.
Figure 3:
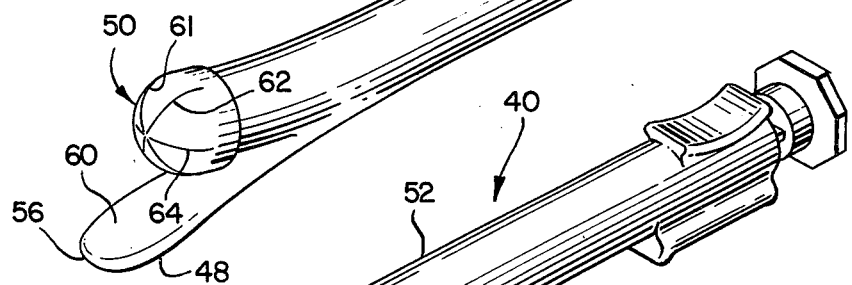
FIG. 3 is a perspective view of the device of FIG. 2 in a second operating condition.
Figure 4:
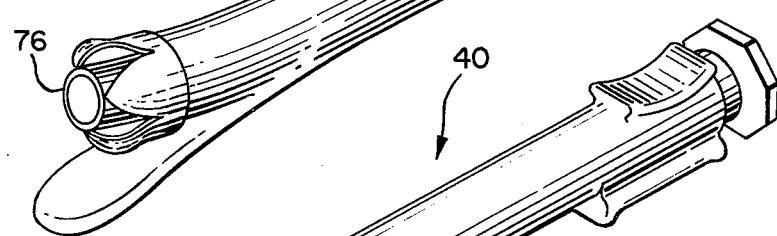
FIG. 4 is a perspective view of the device of FIG. 2 in a third operating condition.

In operation, first device 40, as shown in FIG. 2, is inserted into the vaginal cavity in such a way that reference foot portion 48 moves continuously along the inferior vaginal wall until the instrument can be inserted no farther. At this point, forward extremity 56 is seated at the end 32 of the posterior fornix, which is the reference point for operation of the instrument. Next, manual pressure is exerted between fingers against grip portion 54 and thumb or palm against handle 72 to cause the peripheral forward edge of test element 76 to abut against and to open the flaps defined by slits 61, 62, 64, as shown in FIG. 3. Next, further manual pressure on handle 72 causes the forward portion of shaft 46 to project from sheath 42 and the forward surface 75 of test element 76 to abut against cervical os 30. Next, shaft 46 is retrieved into sheath 42 to retract test element 76 into sheath 42. Finally, the entire device is removed from the vaginal cavity. The arrangement is such that test element 76 now can be removed from shaft 46 in such a way as to permit cervical mucus thereon to be tested.

Since certain changes may be made in the foregoing disclosure without departing from scope of the invention hereof, it is intended that all matter described in the foregoing specification or shown in the accompanying drawings be interpreted in an illustrative and not in a limiting sense.

What is claimed is:
1. A vaginal probe comprising:
 (a) sheath means characterized substantially by an original shape extending substantially along an axis of elongation for insertion into the vaginal cavity, said sheath means including forward extremity means connected thereto and intermediate mouth means, said sheath means being sufficiently rigid to provide a passage therethrough and to substantially maintain said original shape during said insertion;
(b) shaft means having a rigid rearward portion and a semi-rigid forward portion for causing closing of said mouth means when in one condition and causing opening of said mouth means when in another condition;
(c) specimen sampling means for confinement within said sheath means when in one condition and for protrusion through said mouth means when in another condition, said specimen sampling means extending through a predetermined region, when in said other condition, from said mouth means to the cervical os;
(d) said specimen means being confined within said sheath means when said sheath means is inserted into and is withdrawn from the vaginal cavity;
(e) a control means, said specimen means being in contact with the cervical os when said extremity means is seated in the posterior fornix, said control means is in one condition so that said mouth means is open, and said specimen means is in one condition so that it protrudes through said mouth means;
(f) said forward extremity means having a configuration for seating in the posterior fornix and being a mechanical reference ranging in length along said axis from 1 to 5 centimeters and maintaining said length along said axis during said insertion.

2. The probe of claim 1 wherein said sheath means defines a path therewithin having a straight rearward portion and a curved forward portion.

3. The probe of claim 1 wherein said mouth means is provided by a cap that is removably connected to the remainder of said sheath means.

4. The probe of claim 1 wherein said shaft means is slidable in said sheath means between an inoperative position at which it is confined within said sheath means and an operative position at which it protrudes through said mouth means.

5. The probe of claim 1 wherein said specimen means includes a test element at its forward extremity, said forward extremity having an inoperative position at which it is confined within said sheath means and an operative position at which it projects from said sheath means.

6. The probe of claim 1 wherein said shaft means includes a flexible intermediate portion having a spine and a plurality of beads, said beads being of substantially the same maximum cross-sectional extent as said passage of said sheath means.

7. The probe of claim 1 wherein said rigid rearward portion has a controlling diameter that is substantially the same as the diameter of said passage of said sheath means.

8. A vaginal probe comprising:
(a) sheath means characterized substantially by an original shape extending substantially along an axis of elongation for insertion into the vaginal cavity, said sheath means including forward extremity means connected thereto and intermediate mouth means, said sheath means being sufficiently rigid to provide a passage therethrough and to substantially maintain said original shape during said insertion;
(b) shaft means having a rearward portion and a forward portion for causing closing of said mouth means when in one condition and causing opening of said mouth means when in another condition;
(c) specimen sampling means at the forward extremity of said shaft means for confinement with said sheath means when in one condition and for protrusion through said mouth means when in another condition, said specimen sampling means extending through a predetermined region, when in said other condition, from said mouth means to the cervical os;
(d) said specimen means being confined within said sheath means when said sheath means is inserted into and is withdrawn from the vaginal cavity;
(e) a control means, said specimen means being in contact with the cervical os when said extremity means is seated in the posterior fornix, said control means is in one condition so that said mouth means is open, and said specimen means is in one condition so that it protrudes through said mouth means;
(f) said forward extremity means having a configuration for seating in the posterior fornix and being a mechanical reference ranging in length along said axis from 1 to 5 centimeters and maintaining said length along said axis during said insertion.

9. The probe of claim 8 wherein said sheath means defines a path therewithin having a straight rearward portion and a curved forward portion.

10. The probe of claim 8 wherein said mouth means is provided by a cap that is removably connected to the remainder of said sheath means.

11. The probe of claim 8 wherein said shaft means is slidable in said sheath means between an inoperative position at which it is confined within said sheath means and an operative position at which it protrudes through said mouth means.

12. The probe of claim 8 wherein said specimen means includes a test element at its forward extremity, said forward extremity having an inoperative position at which it is confined within said sheath means and an operative position at which it projects from said sheath means.

13. The probe of claim 8 wherein said shaft means includes a flexible intermediate portion having a spine and a plurality of beads, said beads being of substantially the same maximum cross-sectional extent as said passage of said sheath means.

14. The probe of claim 8 wherein said rigid rearward portion has a controlling diameter that is substantially the same as the diameter of said passage of said sheath means.

* * * * *